(12) United States Patent
Wu et al.

(10) Patent No.: US 11,501,430 B2
(45) Date of Patent: Nov. 15, 2022

(54) HEART RATE MEASUREMENT USING VIDEO

(71) Applicant: UNIVERSITY OF MARYLAND, COLLEGE PARK, College Park, MD (US)

(72) Inventors: Min Wu, Clarksville, MD (US); Chau-Wai Wong, Raleigh, NC (US); Qiang Zhu, College Park, MD (US); Chang-Hong Fu, JiangSu (CN); Jiahao Su, College Park, MD (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 36 days.

(21) Appl. No.: 16/647,233

(22) PCT Filed: Sep. 17, 2018

(86) PCT No.: PCT/US2018/051342
§ 371 (c)(1),
(2) Date: Mar. 13, 2020

(87) PCT Pub. No.: WO2019/055919
PCT Pub. Date: Mar. 21, 2019

(65) Prior Publication Data
US 2021/0082109 A1    Mar. 18, 2021

Related U.S. Application Data

(60) Provisional application No. 62/559,182, filed on Sep. 15, 2017.

(51) Int. Cl.
*G06K 9/00* (2022.01)
*A61B 5/02* (2006.01)
(Continued)

(52) U.S. Cl.
CPC ........ *G06T 7/0012* (2013.01); *A61B 5/02416* (2013.01); *A61B 5/1032* (2013.01);
(Continued)

(58) Field of Classification Search
USPC ........ 382/100, 103, 106–108, 117–118, 140, 382/162–167, 168, 181, 199, 209, 219,
(Continued)

(56) References Cited

U.S. PATENT DOCUMENTS

| | | | |
|---|---|---|---|
| 2013/0245462 A1* | 9/2013 | Capdevila | G06T 7/0012 600/479 |
| 2016/0106329 A1* | 4/2016 | Hoof | A61B 5/0013 600/479 |

(Continued)

OTHER PUBLICATIONS

International Search Report is and Written Opinion dated Jan. 16, 2019 corresponding to International Patent Application No. PCT/US2018/051342.

*Primary Examiner* — Seyed H Azarian
(74) *Attorney, Agent, or Firm* — Squire Patton Boggs (US) LLP

(57) ABSTRACT

Systems, methods, apparatuses, and computer program products for contact-free heart rate monitoring and/or measurement are provided. One method may include receiving video(s) that include visual frame(s) of individual s) performing exercises, detecting some exposed skin from the video(s), and performing motion compensation to generate color signals for the exposed skin to precisely align frames of the exposed skin. The method may also include generating the color signals by estimating a skin color for each frame by taking a spatial average over pixels of a cheek of the face(s) for R, G, and B channels, respectively, applying an operation to remove remaining motion traces from the frames such that the heart rate traces dominate, and extract- (Continued)

ing and/or outputting the heart rate of the individuals using a frequency estimator of the skin color signals.

18 Claims, 5 Drawing Sheets

(51) Int. Cl.
*G06T 7/00* (2017.01)
*G06T 7/269* (2017.01)
*G06T 7/90* (2017.01)
*A61B 5/024* (2006.01)
*A61B 5/103* (2006.01)
*A61B 5/00* (2006.01)
*A63B 24/00* (2006.01)

(52) U.S. Cl.
CPC .............. *A61B 5/441* (2013.01); *A61B 5/725* (2013.01); *A61B 5/7207* (2013.01); *A63B 24/0062* (2013.01); *G06T 7/269* (2017.01); *G06T 7/90* (2017.01); *A63B 2220/05* (2013.01); *A63B 2220/806* (2013.01); *A63B 2230/06* (2013.01); *G06T 2207/10016* (2013.01); *G06T 2207/30048* (2013.01); *G06T 2207/30088* (2013.01); *G06T 2207/30201* (2013.01)

(58) Field of Classification Search
USPC ....... 382/224, 254, 274, 276, 286, 305, 321; 600/479
See application file for complete search history.

(56) References Cited

U.S. PATENT DOCUMENTS

2016/0278644 A1\* 9/2016 He ........................ A61B 5/7275
2016/0317041 A1\* 11/2016 Porges ................ A61B 5/7235
2017/0238805 A1\* 8/2017 Addison .............. A61B 5/0205

\* cited by examiner

HEART RATE MEASUREMENT USING VIDEO

CROSS-REFERENCE TO RELATED APPLICATIONS

This application claims priority from U.S. provisional patent application No. 62/559,182 filed on Sep. 15, 2017. The contents of this earlier filed application are hereby incorporated in their entirety.

GOVERNMENT SUPPORT

This invention was made with government support under ECCS1309623 & CCF1320803 awarded by NSF. The government has certain rights in the invention.

FIELD

Some example embodiments may relate to methods, apparatuses and/or systems for contact-free monitoring of heart rate(s) using videos of people.

BACKGROUND

Heart monitoring or cardiac monitoring generally includes intermittent or continuous monitoring of heart activity or rhythm In most instances, cardiac monitoring is performed by electrocardiography that includes recording the electrical activity of the heart over a period of time using electrodes placed over the skin. The electrodes are able to detect the electrical changes on the skin that arise from the heart's electrophysiologic pattern during each heartbeat. Other heart rate monitors, such as chest belts, finger clips or smart watches, can monitor heart rate by contacting different parts of an individual's body.

More recently, contact-free methods for monitoring heart rate have been developed. These methods can be a more user-friendly approach than conventional contact based methods, such as electrodes, chest belts, or finger clips. However, thus far, contact-free heart rate monitoring has not been sufficiently accurate for capturing heart rates using videos of human faces.

SUMMARY

One embodiment is directed to a method for contact-less measurement of heart rate. The method may include receiving one or more video(s) that may include visual frames of one or more individual(s) performing exercises, detecting at least some exposed skin from the individual(s) in the video(s), and performing motion compensation to generate skin color signals for the detected exposed skin. In an embodiment, the performing of the motion compensation comprises performing motion compensation for precisely aligning frames of the detected exposed skin. The method may also include generating the skin color signals using the precisely aligned frames of the detected exposed skin, where the generating comprises estimating a skin color for each frame by taking a spatial average over pixels of at least a portion of the exposed skin for R, G, and B channels, respectively. The method may then include applying an operation to remove remaining motion traces from the frames such that the heart rate traces dominate, and extracting and/or outputting the heart rate of the individuals using a frequency estimator of the skin color signals.

Another embodiment is directed to an apparatus for contact-less measurement of heart rate. The apparatus may include at least one processor and at least one memory comprising computer program code. The at least one memory and computer program code may be configured, with the at least one processor, to cause the apparatus at least to receive one or more video(s) that may include visual frames of one or more individual(s) performing exercises, detect at least some exposed skin from the individual(s) in the video(s), and perform motion compensation to generate skin color signals for the detected exposed skin. In an embodiment, the performing of the motion compensation comprises performing motion compensation for precisely aligning frames of the detected exposed skin. The at least one memory and computer program code may be configured, with the at least one processor, to cause the apparatus at least to generate the skin color signals using the precisely aligned frames of the detected exposed skin, where the generating comprises estimating a skin color for each frame by taking a spatial average over pixels of at least a portion of the exposed skin for R, G, and B channels, respectively. The at least one memory and computer program code may be configured, with the at least one processor, to cause the apparatus at least to apply an operation to remove remaining motion traces from the frames such that the heart rate traces dominate, and extract and/or output the heart rate of the individuals using a frequency estimator of the skin color signals.

Another embodiment is directed to an apparatus for contact-less measurement of heart rate. The apparatus may include receiving means for receiving one or more video(s) that may include visual frames of one or more individual(s) performing exercises, detecting means for detecting at least some exposed skin from the individual(s) in the video(s), and performing means for performing motion compensation to generate skin color signals for the detected exposed skin. In an embodiment, the performing means comprises means for performing motion compensation for precisely aligning frames of the detected exposed skin. The apparatus may also include generating means for generating the skin color signals using the precisely aligned frames of the detected exposed skin, where the generating means comprises means for estimating a skin color for each frame by taking a spatial average over pixels of at least a portion of the exposed skin for R, G, and B channels, respectively. The apparatus may also include applying means for applying an operation to remove remaining motion traces from the frames such that the heart rate traces dominate, and extracting means for extracting and/or outputting the heart rate of the individuals using a frequency estimator of the skin color signals.

Another embodiment is directed to computer readable medium comprising program instructions stored thereon for performing a method. The method may include receiving one or more video(s) that may include visual frames of one or more individual(s) performing exercises, detecting at least some exposed skin from the individual(s) in the video(s), and performing motion compensation to generate skin color signals for the detected exposed skin. In an embodiment, the performing of the motion compensation comprises performing motion compensation for precisely aligning frames of the detected exposed skin. The method may also include generating the skin color signals using the precisely aligned frames of the detected exposed skin, where the generating comprises estimating a skin color for each frame by taking a spatial average over pixels of at least a portion of the exposed skin for R, G, and B channels, respectively. The method may then include applying an operation to remove remaining motion traces from the frames such that the heart rate traces dominate, and extracting and/or outputting the heart rate of the individuals using a frequency estimator of the skin color signals.

BRIEF DESCRIPTION OF THE DRAWINGS

For proper understanding of example embodiments, reference should be made to the accompanying drawings, wherein.

DETAILED DESCRIPTION

Figure 1:
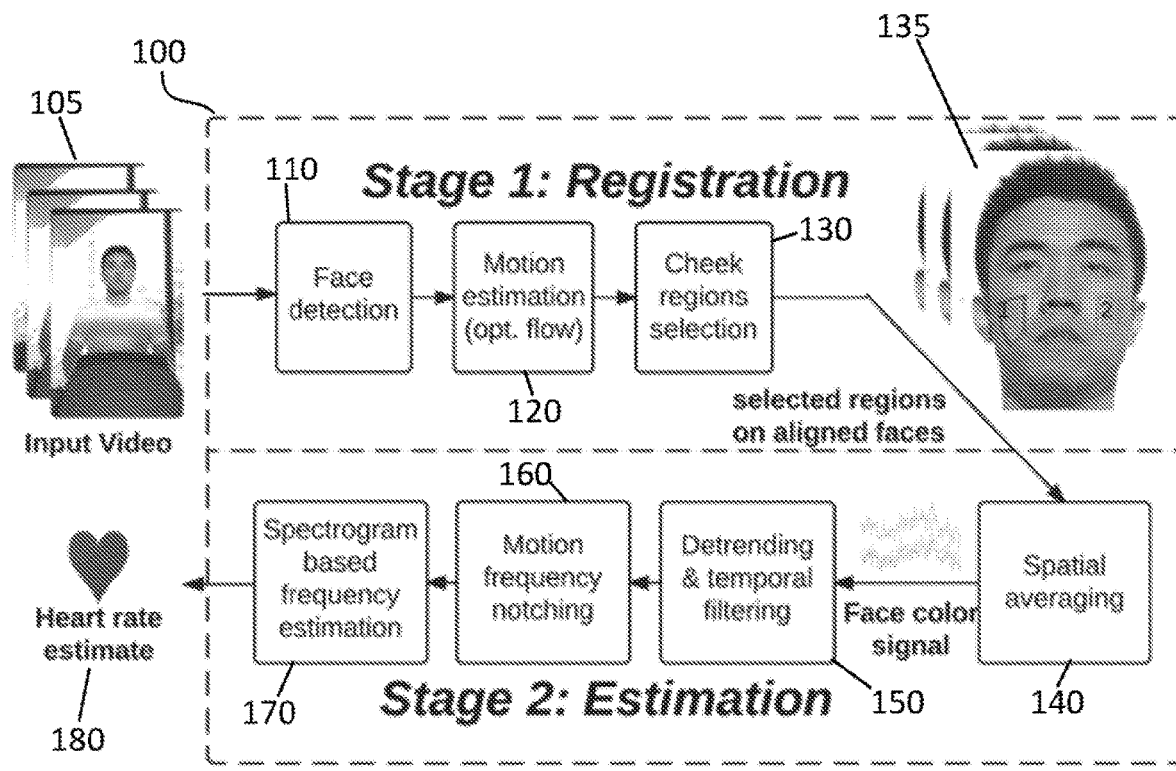
FIG. 1 illustrates an example block diagram of a heart rate monitoring system 100, according to an example embodiment.

It will be readily understood that the components of certain example embodiments, as generally described and illustrated in the figures herein, may be arranged and designed in a wide variety of different configurations. Thus, the following detailed description of some example embodiments of systems, methods, apparatuses, and computer program products for contact-free heart rate monitoring, is not intended to limit the scope of certain embodiments but is representative of selected example embodiments.

The features, structures, or characteristics of example embodiments described throughout this specification may be combined in any suitable manner in one or more example embodiments. For example, the usage of the phrases "certain embodiments," "some embodiments," or other similar language, throughout this specification refers to the fact that a particular feature, structure, or characteristic described in connection with an embodiment may be included in at least one embodiment. Thus, appearances of the phrases "in certain embodiments," "in some embodiments," "in other embodiments," or other similar language, throughout this specification do not necessarily all refer to the same group of embodiments, and the described features, structures, or characteristics may be combined in any suitable manner in one or more example embodiments.

Additionally, if desired, the different functions or steps discussed below may be performed in a different order and/or concurrently with each other. Furthermore, if desired, one or more of the described functions or steps may be optional or may be combined. As such, the following description should be considered as merely illustrative of the principles and teachings of certain example embodiments, and not in limitation thereof.

Contact-free monitoring of the heart rate using videos of human faces or other exposed skin is a user-friendly approach compared to conventional contact based ones, such as the use of electrodes, chest belts, and/or finger clips. Such contact-free monitoring systems can extract, from a video of an individual's face, a 1-D sinusoid-like face color signal that has the same frequency as the individual's heartbeat. Thus, the ability to measure heart rate without touch-based sensors is an attractive approach and has the potential for beneficial applications in areas such as smart health and sports medicine.

To this point, measuring heart rate from videos has mostly focused on still or rest cases, or situations with relatively small body motions. In contrast, there has been little focus on measuring heart rate in large motion scenarios, such as during fitness exercises. Although it has been shown that, after using block-based motion estimation for an exercise video, a periodic signal can be extracted from the color in the face area. However, this was not verified against a reference signal and the accuracy of the estimated heart rate was not quantitatively determined.

According to certain example embodiments, a contactless heart rate measurement system, apparatus and/or method are provided. Some embodiments may be used, for example, to extrapolate or determine a person's heart rate from videos of fitness exercises. An embodiment may be configured to capture possibly wildly varying heart rate through different stages of fitness exercises.

FIG. 1 illustrates an example block diagram of a heart rate monitoring system 100, according to an example embodiment. In an embodiment, the system 100 may take one or more videos 105 as an input. The video(s) 105 may include fitness or exercise videos one or more facial images, or images of other exposed skin, of a person. Fitness exercise videos may contain large and periodic motions. An embodiment provides a highly precise motion compensation scheme to allow generating a clean skin color signal or face color signal to facilitate latter analysis steps, and may use the resulting motion cue as a guide to adaptively remove ambiguous frequency components that can be substantially close to the heart rate. It is noted that certain embodiments discussed in the following utilize an individual's face as an example of exposed skin that can be utilized in the steps for measuring a person's heart rate. However, it should be understood that other embodiments are equally applicable to any exposed skin of a person's body part (not just the face). As such, example embodiments are not merely limited to detection and processing of the individual's face, but is similarly applicable to other body parts.

As illustrated in the example of FIG. 1, system 100 may include a face detection block 110 configured to detect face(s) (or other exposed skin) from the input video(s) 105. In an embodiment, system 100 may also include a motion estimation block 120 configured to perform highly precise pixel-level motion compensation. This precise pixel-level motion compensation is one important step toward generating a clean face color signal. In one embodiment, motion estimation block 120 may use an optical flow algorithm to find correspondences of all points on the faces between two frames. Optical flow uses gradient information to iteratively refine the estimated motion vector field.

In order to avoid being trapped in local optima, an embodiment may introduce a pre-alignment stage to bring the face images roughly aligned before conducting a fine-grain alignment using optical flow. Certain example embodiments may utilize the Viola-Jones face detector to obtain rough estimates of the location and size of the face. An example embodiment may clip and resize the face region of each frame, for example to 180 pixels in height, effectively generating a pre-aligned video for the face region. The pre-alignment may significantly reduce the lengths of motion vectors, which in turn makes results of optical flow more reliable. In one example, two face images may be likely to have a global color difference due to the heartbeat. In order to conduct a precise face alignment, instead of using the illumination consistency assumption that is widely used, an embodiment assumes more generally that the intensity I of a point in two frames are related by an affine model, namely:

$$I(x+\Delta x, y+\Delta y, t+1) = (1-\epsilon)I(x,y,t)+b \quad (1)$$

where $\epsilon$ and b control the scaling and bias of the intensities between two frames. Both of them are usually small. Traditional techniques tackling the illumination consistency cases such as Taylor expansion and regularization can be similarly applied, according to certain embodiments. Mathematical analysis has shown that omitting the illumination change due to the heartbeat, and applying a standard optical flow method leads to a bias term that is at the same (or similar) order magnitude compared to the intrinsic error (in terms of standard deviation) of the optical flow system.

Figure 2:
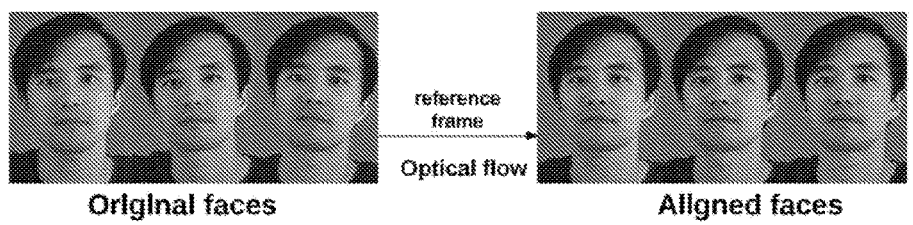
FIG. 2 illustrates an example of face images from a same segment before and after optical flow based motion compensation using the same reference, according to an example embodiment.

According to certain embodiments, each video may be divided into small temporal segments with one frame overlapping for successive segments. In an embodiment, the frame in the middle of the segment may be used as the reference for optical flow based motion compensation. This would ensure that two frames being aligned do not have significant occlusion due to long separation in time. FIG. 2 illustrates an example of face images from a same segment before and after optical flow based motion compensation using the same reference, according to an example embodiment.

As illustrated in the example of FIG. 1, system 100 may also include a segment continuity and cheek regions selection block 130 configured to select cheek regions and/or corresponding face landmarks. With precisely aligned face videos in short segments, an embodiment can estimate the face color for each frame by taking a spatial average over pixels of the cheek for R, G, and B channels, respectively. The three resulting 1-D time signals may be referred to as the face color signals.

When concatenating segments into color signals, the last point of the current segment and the first point of the next segment may have different intensities because they correspond to the same frame whose motion compensation were conducted with respect to two different references. To address this problem, according to an embodiment, the difference of the intensity between the two points may be calculated and the resulting value is used to bias the signal of the next segment in order to maintain the continuity. The face color signals may contain color change due to the heartbeat, and illumination change due to face motions such as tilting. In an embodiment, the green channel may be used because it corresponds to the absorption peak of (oxy-)hemoglobin that changes periodically as the heartbeat, and source separation methods such as the independent component analysis (ICA) may also be used to separate the heartbeat component. According to an embodiment, the fixed linear weights (−1,2,−1) may be used for R, G, B channels to best retain the heartbeat component while compensating the motion induced illumination change.

To determine the cheek regions for conducting spatial averaging 140, an example embodiment may construct two conservative regions that do not contain facial structures and are most upfront in order to avoid strong motion-induced specular illumination changes. Certain embodiments may then use identified facial landmarks to facilitate the construction of the cheek regions. In one embodiment, each cheek region may be constructed to be a polygon that has a safe margin to the facial structures protected by the landmarks. One example for such selected cheek regions and corresponding face landmarks is depicted on the face 135 illustrated in FIG. 1.

As further illustrated in the example of FIG. 1, system 100 may also include a de-trending and temporal filtering block 150 that may be configured to take the face color signal as input and remove illumination variation. It is noted that illumination variation can be caused by passersby and/or the gradual change of sun light, for example, which can result in the face color signal to drift. This can be problematic for Fourier-based analysis. Such slowly-varying trend can be estimated and then subtracted from a raw face color signal, $x_{raw} \in R^L$, where L is the length of the signal. The trend may be assumed to be a clean, unknown version of $x_{raw}$ with a property that its accumulated convexity measured for every point on the signal is as small as possible, namely:

$$\hat{x}_{trend} = \underset{x}{\operatorname{argmin}} \; \|x_{raw} - x\|^2 + \lambda \|D_2 x\|^2 \quad (2)$$

where $\lambda$ is a regularization parameter controlling the smoothness of the estimated trend, and $D_2 \in R^{L \times L}$ is a spare toeplitz second-order difference matrix. The closed-form solution is $\hat{x}_{trend} = (I + \lambda D_2^T D_2)^{-1} x_{raw}$. Hence, the detrended signal is $x_{raw} - \hat{x}_{trend}$. After detrending, an embodiment may use a bandpass filter to reject the frequency components that are outside a normal range of human heart rate. In one example, the bandpass filter may be an IIR Butterworth with a passband from 40 to 240 bpm. In an embodiment, adaptive filtering may be applied using the analyzed motion information to mitigate the motion effect and output a signal containing the human heart rate trace with an improved signal-to-noise ratio.

In the above-described stages of the system 100 of FIG. 1, the impact of face motions is removed. For example, optical flow can be used to precisely align the faces, and a color weight vector that is least susceptible to motion may be used to reduce impact of the periodic illumination change, for example, due to the face tilting. As also illustrated in the example of FIG. 1, system 100 further includes a motion frequency notching block 160 that may be configured to apply a notching operation to remove any remaining trace due to motion. In an embodiment, motion information from the face tracker and the optical flow may be combined to generate two time signals, one for the x-direction and the other for the y-direction. For each time bin on the spectrogram, one embodiment may conduct two notch operations based on the dominating frequency estimated from the x- and y-motion components.

Figure 3:
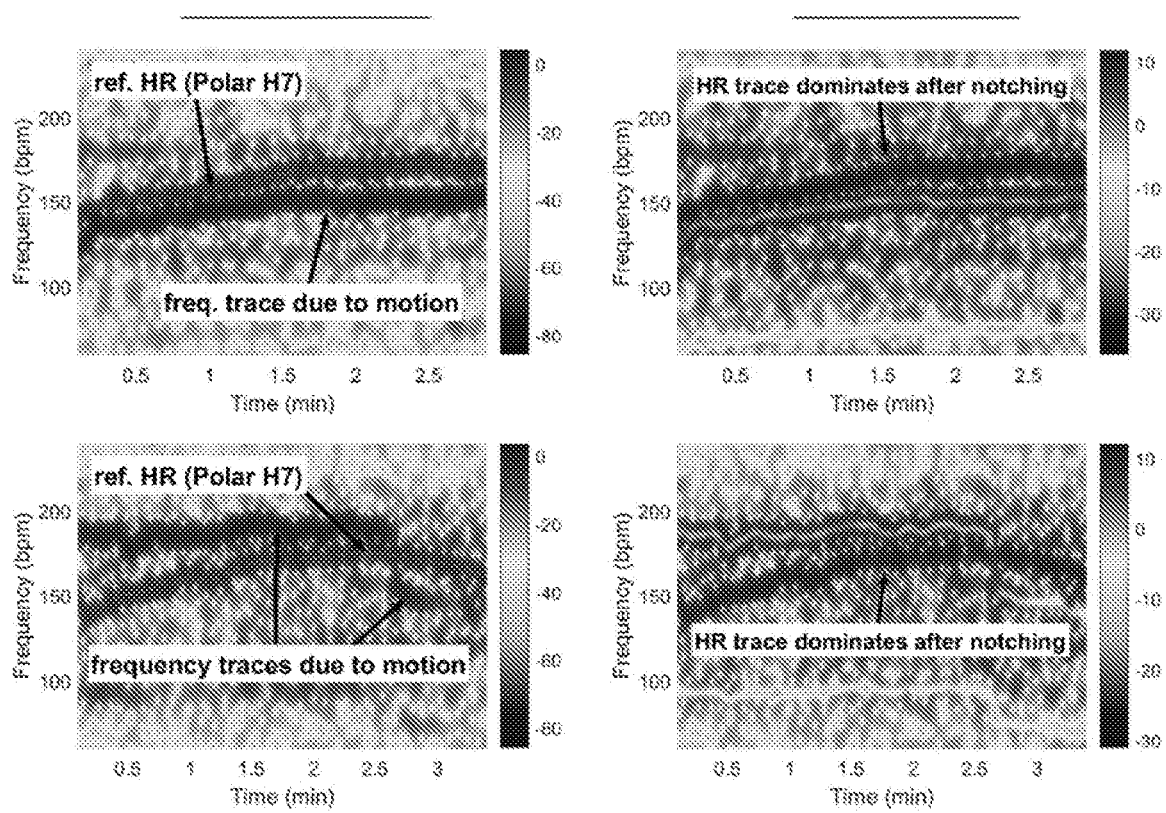
FIG. 3 illustrates an example of the contrast of spectrograms before and after notching the frequencies of fitness motions, according to certain embodiments.

FIG. 3 illustrates an example of the contrast of spectrograms before and after notching the frequencies of fitness motions, according to certain embodiments. Spectrograms in the left column of FIG. 3 show that motion traces exist before notching, as highlighted by the arrows. Motion artifacts can be even stronger than the heart rate (HR) traces. Spectrograms in the right column of FIG. 3 show that the frequency notching method according to certain embodiments is effective in removing motion trace, as the HR traces dominate after notching.

As also illustrated in FIG. 1, system 100 may also include a spectrogram based frequency estimation block 170 configured to output an estimate of the heart rate. In an embodiment, frequency estimation block 170 may include a robust frequency estimator for noisy face color signals from fitness exercises. Instead of directly finding the peak (the mode) of the power spectrum for every time bin that may result in a discontinuous estimated heart-rate signal, one embodiment may construct a two-step process to ensure the estimated signal is smooth. In an embodiment, a single most probable strap is selected from the spectrogram, and each time bin of the spectrogram image may be binarized per the 95th percentile of the power spectrum of that bin. An embodiment may then dilate and erode the image in order to connect the broken strap. The largest connected region may be found using a traverse algorithm such as the breadth-first search and is considered as the most probable strap.

Figure 4A:
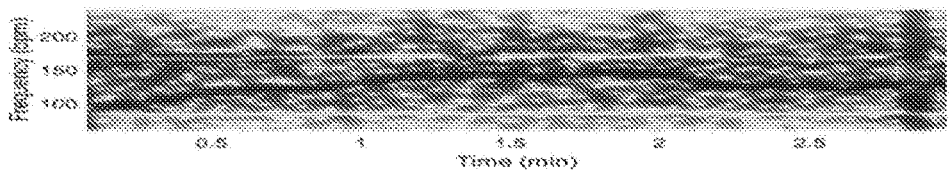
FIG. 4a illustrates an example of spectrogram results with weakly connected frequency strap.
Figure 4B:
FIG. 4b illustrates an example of spectrogram results after the operations of binarization using, dilation and erosion, and small regions removal, according to certain embodiments.

FIG. 4 illustrates an example of spectrogram results according to the steps of FIG. 1. More specifically, FIG. 4a illustrates a spectrogram with weakly connected frequency strap, and FIG. 4b illustrates the results after the operations of binarization using 95$^{th}$ percentile, dilation and erosion, and small regions removal, according to certain embodiments.

An embodiment may then use a weighted frequency within the frequency range specified by the strap, $F_i$, as the frequency estimate for ith time bin. Denoting the frequency estimate as $\hat{f}_{HR}(i)$ according to the following:

$$\hat{f}_{HR}(i) = \sum_{f \in F_i} w_{i,f} * f$$

where $$w_{i,f} = |S(i, f)| / \sum_{f \in F_i} |S(i, f)|,$$

and S(i, :) is the power spectrum at the ith bin.

Thus, according to the example embodiment of FIG. 1, red green blue (RGB) weights may be used to resist unwanted illumination changes due to motion. The registration error may be minimized using pixel-level optical flow based motion compensation that is capable of generating almost "frozen" videos for best extracting the face color signals. De-trending may be used to remove the illumination variation caused by passersby and/or the gradual change of sun light that can cause problems for frequency estimation. Notching operations may be applied to remove frequency traces caused by periodic motion of fitness exercises with the help of motion information from the face tracker and the optical flow. A robust spectrogram based frequency estimator may then be applied to extract the final heart rate trace.

Figure 5:
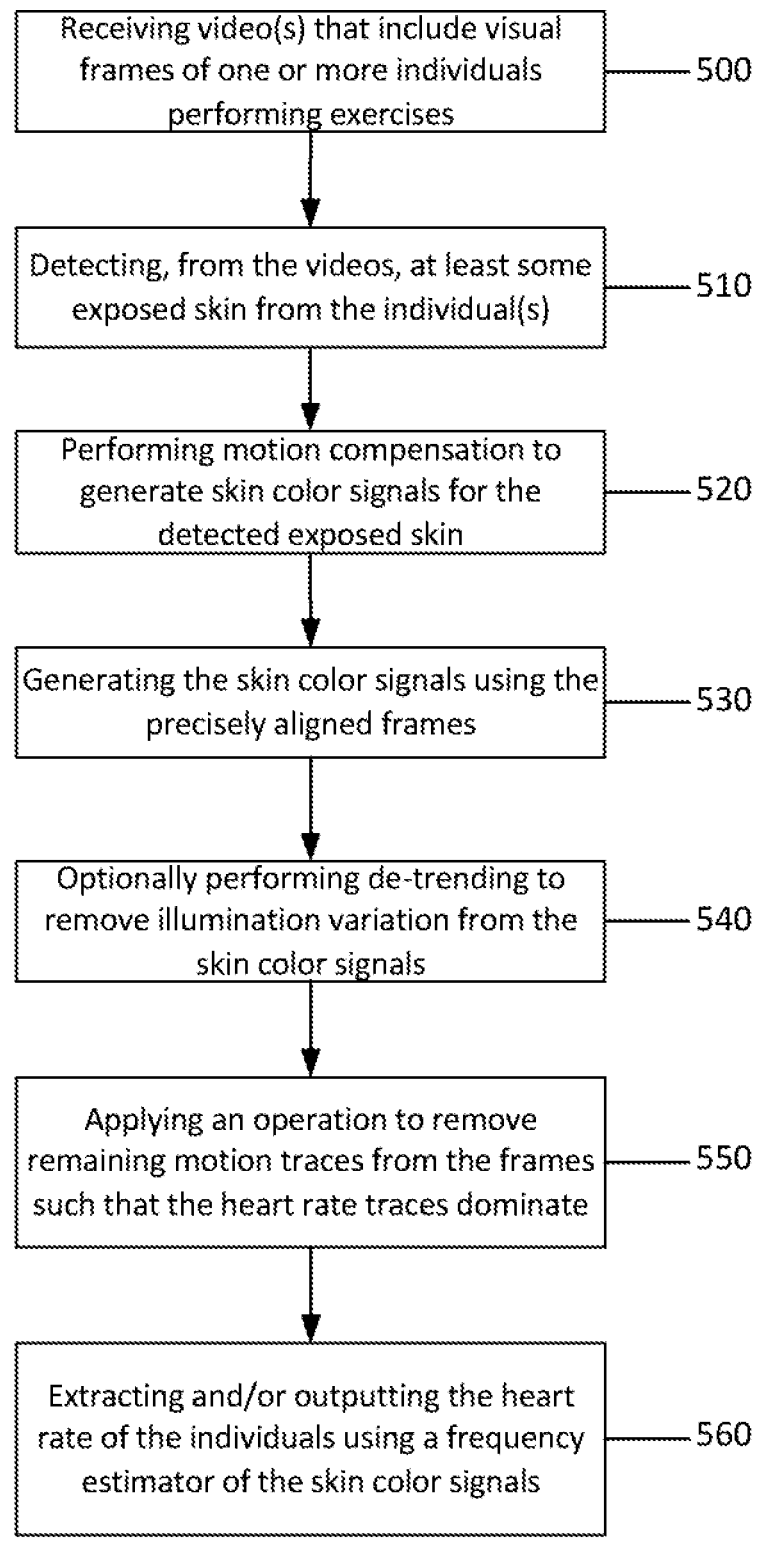
FIG. 5 illustrates an example flow diagram of a process for contact-less measurement of heart rate, according to an example embodiment.

FIG. 5 illustrates an example flow diagram of a method or process for contact-less measurement of heart rate, according to an example embodiment. In certain embodiments, the method of FIG. 5 may be performed by the system of FIG. 1 discussed above. As illustrated in the example of FIG. 5, the method may include, at 500, receiving or capturing one or more fitness or exercise videos that may include visual frames or images of one or more individuals performing exercises or other physical activity. According to certain embodiments, the method may then include, at 510, detecting at least some portion of exposed skin of the individual(s) in the video(s). In one embodiment, the exposed skin may include one or more face(s) of the individual(s) from the fitness videos.

In an embodiment, the method may also include, at 520, performing (pixel-level) motion compensation in order to generate skin color signals for the detected exposed skin. In an embodiment, the skin color signals may be face color signals. According to one embodiment, the performing of the motion compensation 520 may include performing optical flow based motion compensation for precisely aligning frames of the face(s). For example, in one embodiment, the performing of the optical flow based motion compensation may include executing an optical flow algorithm to find correspondences of all points on the face(s) between two frames of the video(s). In one example, optical flow uses gradient information to iteratively refine the estimated motion vector field. According to an embodiment, in order to avoid being trapped in local optima, the performing of the motion compensation 520 may include may include performing a pre-alignment step to bring the face images roughly aligned before conducting the optical flow based motion compensation to obtain the fine-grain alignment. In an example embodiment, the pre-alignment step may include utilizing a Viola-Jones face detector to obtain rough estimates of the location and size of the face(s), and clipping and resizing the face region of each frame to 180 pixels in height, in order to effectively generate a pre-aligned video for the face region. The pre-alignment step may significantly reduce the lengths of motion vectors, which in turn makes results of optical flow more reliable. In one example, two face images may be likely to have a global color difference due to the heartbeat. In order to conduct a precise face alignment, in one embodiment, the performing of the motion compensation 520 may include assuming that the intensity I of a point in two frames are related by an affine model, namely:

$$I(x+\Delta x, y+\Delta y, t+1) = (1-\epsilon)I(x,y,t)+b \quad (1)$$

where $\epsilon$ and b control the scaling and bias of the intensities between two frames. Traditional techniques tackling the illumination consistency cases such as Taylor expansion and regularization can be similarly applied, according to certain embodiments.

According to certain embodiments, the performing of the motion compensation 520 may include dividing each video into small temporal segments with one frame overlapping for successive segments. In an embodiment, the frame in the middle of the segment may be used as the reference for optical flow based motion compensation. This would ensure that two frames being aligned do not have significant occlusion due to long separation in time.

Continuing with the example illustrated in FIG. 5, the method may further include, at 530, generating the skin color signals (or face color signals), for example, using the precisely aligned frames of the face(s) (produced from the motion compensation step 520). In an embodiment, the generating of the skin color signals 530 may include estimating a skin or face color for each frame by taking a spatial average over pixels of a cheek of the face(s) for the R, G, and B channels, respectively. According to some embodiments, the generating of the skin color signals 530 may include concatenating segments of the video(s) into color signals. When concatenating the segments, in an embodiment, the last point of the current segment and the first point of the next segment may have different intensities because they correspond to the same frame whose motion compensation were conducted with respect to two different references.

Thus, according to an embodiment, the generating of the skin color signals 530 may include calculating the difference of the intensity between the two points and using the resulting value to bias the signal of the next segment in order to maintain the continuity. The skin or face color signals may contain color change due to the heartbeat, and illumination change due to face motions such as tilting. In an embodiment, the green channel may be used because it corresponds to the absorption peak of (oxy-) hemoglobin that changes periodically as the heartbeat, and source separation methods such as ICA may also be used to separate the heartbeat component. According to an embodiment, the generating of the skin color signals 530 may include using the fixed linear weights (−1,2,−1) for R, G, B channels to best retain the heartbeat component while compensating for the motion induced illumination change.

In an embodiment, the generating of the skin color signals 530 may further include determining the cheek regions of the face(s), or regions of other exposed skin, for conducting spatial averaging. In one example, the determining of the cheek regions may include constructing two conservative regions that do not contain facial structures and are most upfront in order to avoid strong motion-induced specular illumination changes. Certain embodiments may then use identified facial landmarks to facilitate the construction of the cheek regions. In one embodiment, each cheek region may be constructed to be a polygon that has a safe margin to the facial structures protected by the landmarks.

As further illustrated in the example of FIG. 5, in one embodiment, the method may also include, at 540, optionally performing de-trending to remove the illumination variation from the face color signals. It is noted that, in some embodiments, the de-trending may not need to be performed when there is little lighting variation. In an embodiment, the de-trending step 540 may take the skin or face color signal as an input and remove illumination variation. It is noted that illumination variation can be caused by passersby and/or the gradual change of sun light, for example, which can result in the skin or face color signal to drift. According to one embodiment, the de-trending step 540 may include estimating the varying trend and then subtracting it from a raw face color signal, $x_{raw} \in R^L$, where L is the length of the signal. The trend may be assumed to be a clean, unknown version of $x_{raw}$ with a property that its accumulated convexity measured for every point on the signal is as small as possible, namely:

$$\hat{x}_{trend} = \underset{x}{\operatorname{argmin}} \; \|x_{raw} - x\|^2 + \lambda \|D_2 x\|^2 \qquad (2)$$

where λ is a regularization parameter controlling the smoothness of the estimated trend, and $D_2 \in R^{L \times L}$ is a spare toeplitz second-order difference matrix. The closed-form solution is $\hat{x}_{trend} = (I + \lambda D_2^T D_2)^{-1} x_{raw}$. Hence, the detrended signal is $x_{raw} - \hat{x}_{trend}$. After the de-trending step 540, an embodiment may use a bandpass filter to reject the frequency components that are outside a normal range of human heart rate.

As also illustrated in the example of FIG. 5, in an embodiment, the method may further include, at 550, applying a an operation to remove remaining motion traces from the frames such that the heart rate traces dominate. According to one embodiment, the operation to remove motion traces may include a motion frequency notching operation and/or an adaptive filtering operation. In an embodiment, a motion frequency notching operation may include combining motion information from the face tracker and the optical flow to generate two time signals, one for the x-direction and the other for the y-direction. For each time bin on the spectrogram, one embodiment may conduct two notch operations based on the dominating frequency estimated from the x- and y-motion components.

In an embodiment, the method may then include, at 560, extracting and/or outputting the heart rate of the individual(s) from the video(s) using a frequency estimator for the face color signals. According one example embodiment, the frequency estimator may be a spectrogram based frequency estimator. In an embodiment, the extracting 560 may include using a robust frequency estimator for noisy face color signals from fitness exercises. Instead of directly finding the peak (the mode) of the power spectrum for every time bin that may result in a discontinuous estimated heart-rate signal, the extracting 560 may include constructing a two-step process to ensure the estimated signal is smooth. In an embodiment, a single most probable strap is selected from the spectrogram, and each time bin of the spectrogram image may be binarized per the 95th percentile of the power spectrum of that bin. An embodiment may then dilate and erode the image in order to connect the broken strap. The largest connected region may be found using a traverse algorithm such as the breadth-first search and is considered as the most probable strap. It is noted that the spectrogram based frequency estimation described above is just one tracking approach, according to some embodiments; other embodiments can work with other tracking techniques that can handle weak and noisy traces.

Figure 6:
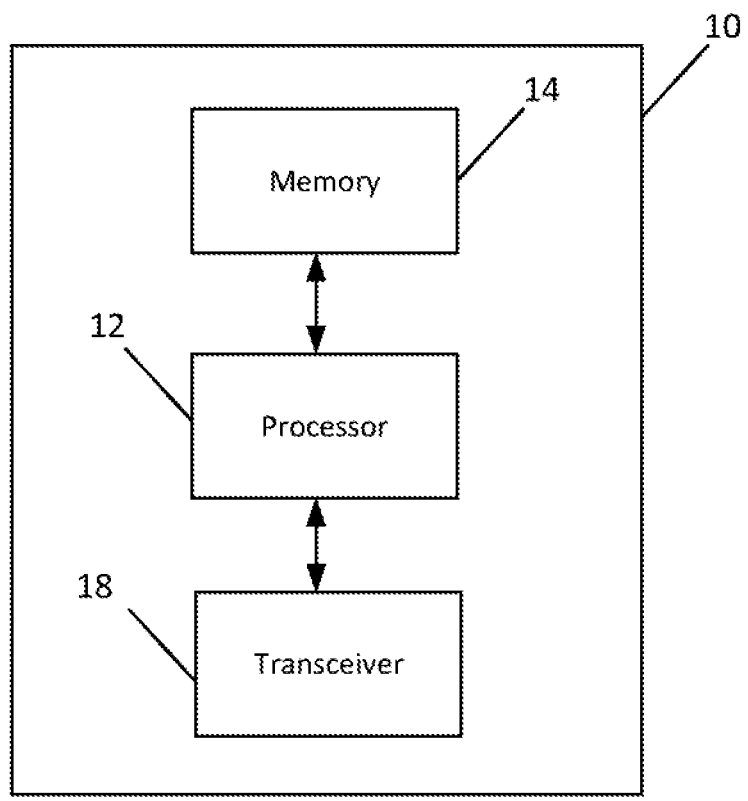
FIG. 6 illustrates an example block diagram of an apparatus, according to an embodiment.

FIG. 6 illustrates an example of an apparatus 10 according to one embodiment. In an example embodiment, apparatus 10 may include a server, computer, or other device capable of executing arithmetic or logical operations. It should be noted that one of ordinary skill in the art would understand that apparatus 10 may include components or features not shown in FIG. 6.

As illustrated in the example of FIG. 6, apparatus 10 may include a processor 12 for processing information and executing instructions or operations. Processor 12 may be any type of general or specific purpose processor. In fact, processor 12 may include one or more of general-purpose computers, special purpose computers, microprocessors, digital signal processors (DSPs), field-programmable gate arrays (FPGAs), application-specific integrated circuits (ASICs), and processors based on a multi-core processor architecture, as examples. In further example embodiments, processor 12 may include a specialized processor or a ML/data analytics based application processor, such as a graphics processing unit (GPU) or tensor processing unit (TPU). In yet a further example, processor 12 may include a neural network or long short term memory (LSTM) architecture or hardware, etc.

While a single processor 12 is shown in FIG. 6, multiple processors may be utilized according to other example embodiments. For example, it should be understood that, in certain example embodiments, apparatus 10 may include two or more processors that may form a multiprocessor system (e.g., in this case processor 12 may represent a multiprocessor) that may support multiprocessing. In certain example embodiments, the multiprocessor system may be tightly coupled or loosely coupled (e.g., to form a computer cluster).

Processor 12 may perform functions associated with the operation of apparatus 10, which may include, for example, executing the process illustrated in the example of FIG. 5.

Apparatus 10 may further include or be coupled to a memory 14 (internal or external), which may be coupled to processor 12, for storing information and instructions that may be executed by processor 12. Memory 14 may be one or more memories and of any type suitable to the local application environment, and may be implemented using any suitable volatile or nonvolatile data storage technology such as a semiconductor-based memory device, a magnetic memory device and system, an optical memory device and system, fixed memory, and/or removable memory. For example, memory 14 can be comprised of any combination of random access memory (RAM), read only memory (ROM), static storage such as a magnetic or optical disk, hard disk drive (HDD), or any other type of non-transitory machine or computer readable media. The instructions stored in memory 14 may include program instructions or computer program code that, when executed by processor 12, enable the apparatus 10 to perform tasks as described herein. In an embodiment, memory 14 may store modules corresponding to the blocks 110, 120, 130, 140, 150, 160, 170 illustrated in the example of FIG. 1.

In an example embodiment, apparatus 10 may further include or be coupled to (internal or external) a drive or port that is configured to accept and read an external computer readable storage medium, such as an optical disc, USB drive, flash drive, or any other storage medium. For example, the external computer readable storage medium may store a computer program or software for execution by processor 12 and/or apparatus 10.

In some example embodiments, apparatus 10 may further include or be coupled to a transceiver 18 configured to transmit and receive information. Additionally or alternatively, in some example embodiments, apparatus 10 may include an input and/or output device (I/O device).

In an example embodiment, memory 14 may store software modules that provide functionality when executed by processor 12. The modules may include, for example, an operating system that provides operating system functionality for apparatus 10. According to certain embodiments, the modules may include a face detection module, motion estimation module, cheek regions selection module, spatial averaging module, de-trending and temporal filtering module, motion frequency notching module, and/or spectrogram based frequency estimation module. The memory may also store one or more functional modules, such as an application or program, to provide additional functionality for apparatus 10. The components of apparatus 10 may be implemented in hardware, or as any suitable combination of hardware and software.

According to some example embodiments, processor 12 and memory 14 may be included in or may form a part of processing circuitry or control circuitry. In addition, in some example embodiments, transceiver 18 may be included in or may form a part of transceiving circuitry.

As introduced above, in example embodiments, apparatus 10 may be a computer, server, or other similar device. According to example embodiments, apparatus 10 may be controlled by memory 14 and processor 12 to perform the functions associated with any of the example embodiments described herein, such as the system or signaling flow diagrams illustrated in FIGS. 1 and 5. For example, in certain embodiments, apparatus 10 may be controlled by memory 14 and processor 12 to perform one or more of the steps illustrated in FIG. 5. In example embodiments, for instance, apparatus 10 may be configured to perform a process for contact-less measurement of heart rates according to the system illustrated in FIG. 1.

Therefore, certain example embodiments provide several technical improvements, enhancements, and/or advantages. Various example embodiments can, for example, provide a highly precise motion compensation scheme with the help of optical flow and use motion information as a cue to adaptively remove ambiguous frequency components for improving heart rate estimates. Experimental results demonstrate that example embodiments can achieve highly precise estimation with an average error of approximately 1.1 beats per minute (BPM) or just 0.58% in relative error.

In some example embodiments, the functionality of any of the methods, processes, signaling diagrams, algorithms or flow charts described herein may be implemented by software and/or computer program code or portions of code stored in memory or other computer readable or tangible media, and executed by a processor.

In some example embodiments, an apparatus may be included or be associated with at least one software application, module, unit or entity configured as arithmetic operation(s), or as a program or portions of it (including an added or updated software routine), executed by at least one operation processor. Programs, also called program products or computer programs, including software routines, applets and macros, may be stored in any apparatus-readable data storage medium and include program instructions to perform particular tasks.

A computer program product may comprise one or more computer-executable components which, when the program is run, are configured to carry out some example embodiments. The one or more computer-executable components may be at least one software code or portions of it. Modifications and configurations required for implementing functionality of an example embodiment may be performed as routine(s), which may be implemented as added or updated software routine(s). Software routine(s) may be downloaded into the apparatus.

As an example, software or a computer program code or portions of it may be in a source code form, object code form, or in some intermediate form, and it may be stored in some sort of carrier, distribution medium, or computer readable medium, which may be any entity or device capable of carrying the program. Such carriers may include a record medium, computer memory, read-only memory, photoelectrical and/or electrical carrier signal, telecommunications signal, and software distribution package, for example. Depending on the processing power needed, the computer program may be executed in a single electronic digital computer or it may be distributed amongst a number of computers. The computer readable medium or computer readable storage medium may be a non-transitory medium.

In other example embodiments, the functionality may be performed by hardware or circuitry included in an apparatus, for example through the use of an application specific integrated circuit (ASIC), a programmable gate array (PGA), a field programmable gate array (FPGA), or any other combination of hardware and software. In yet another example embodiment, the functionality may be implemented as a signal, a non-tangible means that can be carried by an electromagnetic signal downloaded from the Internet or other network.

According to an example embodiment, an apparatus, such as a node, device, or a corresponding component, may be configured as circuitry, a computer or a microprocessor, such as single-chip computer element, or as a chipset, including at least a memory for providing storage capacity used for arithmetic operation and an operation processor for executing the arithmetic operation.

One having ordinary skill in the art will readily understand that the example embodiments as discussed above may be practiced with steps in a different order, and/or with hardware elements in configurations which are different than those which are disclosed. Therefore, although some embodiments have been described based upon these example preferred embodiments, it would be apparent to those of skill in the art that certain modifications, variations, and alternative constructions would be apparent, while remaining within the spirit and scope of example embodiments. In order to determine the metes and bounds of the example embodiments, therefore, reference should be made to the appended claims.

We claim:

1. A method for contact-less measurement of heart rate, the method comprising:
   receiving one or more videos that include visual frames of one or more individuals;
   detecting at least some exposed skin from the individuals in the videos;
   performing motion compensation to generate skin color signals for the detected exposed skin, wherein the performing of the motion compensation comprises performing motion compensation for precisely aligning frames of the detected exposed skin;
   generating the skin color signals using the precisely aligned frames of the detected exposed skin, wherein the generating comprises estimating a skin color for each frame by taking a spatial average over pixels of at least a portion of the exposed skin for R, G, and B channels, respectively;
   applying an operation to remove remaining motion traces from the frames such that traces of the heart rate dominate; and
   extracting and outputting the heart rate of the individuals using a frequency estimator of the skin color signals,
   wherein the performing of the motion compensation comprises performing optical flow based motion compensation to precisely align the frames of the exposed skin,
   wherein the performing of the optical flow based motion compensation comprises at least one of: finding correspondences of some or all points on the at least one face between two frames of the videos, or dividing each of the videos into temporal segments and using a frame in the temporal segments as a reference for the optical flow based motion compensation.

2. The method according to claim 1, wherein said at least some exposed skin comprises at least one face, wherein the skin color signals comprise face color signals, and wherein said at least a portion of the exposed skin comprises a cheek of the at least one face.

3. The method according to claim 2,
   wherein the face color signals comprise color change due to heartbeat and illumination change due to face motions,
   wherein the generating of the face color signals comprises using fixed linear weights for R, G, and B channels to retain a heartbeat component of the face color signals while compensating for the illumination change.

4. The method according to claim 2, wherein the generating of the face color signals comprises determining cheek regions for conducting spatial averaging by constructing two regions of the at least one face that do not contain facial structures and are most upfront in order to avoid motion induced specular illumination changes.

5. The method according to claim 1, further comprising performing de-trending to remove illumination variation from the skin color signals.

6. The method according to claim 5, wherein the performing of the de-trending comprises using a filter to reject frequency components that are outside a normal range of human heart rate.

7. The method according to claim 1, wherein the applying of the operation to remove the remaining motion traces from the frames comprises applying at least one of a motion frequency notching operation or adaptive filtering operation.

8. The method according to claim 1, further comprising:
   performing a pre-alignment step to make images of the at least one face roughly aligned before performing the optical flow based motion compensation to precisely align the at least one face,
   wherein the pre-alignment step comprises using a face detector to obtain estimates of a location and size of the at least one face, clipping and re-sizing a face region of each frame to generate a pre-aligned video for the face region.

9. An apparatus for contact-less measurement of heart rate, the apparatus comprising:
   at least one processor; and
   at least one memory comprising computer program code,
   the at least one memory and computer program code configured, with the at least one processor, to cause the apparatus at least to
   receive one or more videos that include visual frames of one or more individuals;
   detect at least some exposed skin from the individuals in the videos;
   perform motion compensation to generate skin color signals for the detected exposed skin, wherein the performing of the motion compensation comprises performing motion compensation for precisely aligning frames of the detected exposed skin;
   generate the skin color signals using the precisely aligned frames of the detected exposed skin, wherein the generating comprises estimating a skin color for each frame by taking a spatial average over pixels of at least a portion of the exposed skin for R, G, and B channels, respectively;
   apply an operation to remove remaining motion traces from the frames such that traces of the heart rate dominate; and
   extract and output the heart rate of the individuals using a frequency estimator of the skin color signals,
   wherein the performing of the motion compensation comprises performing optical flow based motion compensation to precisely align the frames of the exposed skin, and
   wherein the at least one memory and computer program code are further configured, with the at least one processor, to cause the apparatus at least to perform at least one of: find correspondences of some or all points on the at least one face between two frames of the videos, or divide each of the videos into temporal segments and use a frame in the temporal segments as a reference for the optical flow based motion compensation.

10. The apparatus according to claim 9, wherein said at least some exposed skin comprises at least one face, wherein the skin color signals comprise face color signals, and wherein said at least a portion of the exposed skin comprises a cheek of the at least one face.

11. The apparatus according to claim 10, wherein the face color signals comprise color change due to heartbeat and illumination change due to face motions.

12. The apparatus according to claim 11, wherein the at least one memory and computer program code are further configured, with the at least one processor, to cause the apparatus at least to generate the face color signals using fixed linear weights for R, G, and B channels to retain a heartbeat component of the face color signals while compensating for the illumination change.

13. The apparatus according to claim 10, wherein the at least one memory and computer program code are further configured, with the at least one processor, to cause the apparatus at least to determine cheek regions for conducting spatial averaging by constructing two regions of the at least one face that do not contain facial structures and are most upfront in order to avoid motion induced specular illumination changes.

14. The apparatus according to claim 9, wherein the at least one memory and computer program code are further configured, with the at least one processor, to cause the apparatus at least to perform de-trending to remove illumination variation from the skin color signals.

15. The apparatus according to claim 9, wherein the applying of the operation to remove the remaining motion traces from the frames comprises applying at least one of a motion frequency notching operation or adaptive filtering operation.

16. The apparatus according to claim 9, wherein the at least one memory and computer program code are further configured, with the at least one processor, to cause the apparatus at least to:
perform a pre-alignment step to make images of the at least one face roughly aligned before performing the optical flow based motion compensation to precisely align the at least one face,
wherein the pre-alignment step comprises using a face detector to obtain estimates of a location and size of the at least one face, clipping and re-sizing a face region of each frame to generate a pre-aligned video for the face region.

17. The apparatus according to claim 9, wherein the at least one memory and computer program code are further configured, with the at least one processor, to cause the apparatus at least to use a filter to reject frequency components that are outside a normal range of human heart rate.

18. A non-transitory computer readable medium comprising program instructions stored thereon for performing at least the following:
receiving one or more videos that include visual frames of one or more individuals;
detecting at least some exposed skin from the individuals in the videos;
performing motion compensation to generate skin color signals for the detected exposed skin, wherein the performing of the motion compensation comprises performing motion compensation for precisely aligning frames of the detected exposed skin;
generating the skin color signals using the precisely aligned frames of the detected exposed skin, wherein the generating comprises estimating a skin color for each frame by taking a spatial average over pixels of at least a portion of the exposed skin for R, G, and B channels, respectively;
applying an operation to remove remaining motion traces from the frames such that traces of the heart rate dominate; and
extracting and outputting the heart rate of the individuals using a frequency estimator of the skin color signals,
wherein the performing of the motion compensation comprises performing optical flow based motion compensation to precisely align the frames of the exposed skin,
wherein the performing of the optical flow based motion compensation comprises at least one of: finding correspondences of some or all points on the at least one face between two frames of the videos, or dividing each of the videos into temporal segments and using a frame in the temporal segments as a reference for the optical flow based motion compensation.

* * * * *